(12) United States Patent
Nallon

(10) Patent No.: US 9,091,652 B2
(45) Date of Patent: Jul. 28, 2015

(54) METHOD OF SENSING NITROAROMATIC ELECTRON ACCEPTING COMPOUNDS USING A PHOTOVOLTAIC SENSOR

(71) Applicant: The United States of America, as represented by the Secretary of the Army, Washington, DC (US)

(72) Inventor: Eric C. Nallon, Woodbridge, VA (US)

(73) Assignee: THE UNITED STATES OF AMERICA AS REPRESENTED BY THE SECRETARY OF THE ARMY, Washington, DC (US)

( * ) Notice: Subject to any disclaimer, the term of this patent is extended or adjusted under 35 U.S.C. 154(b) by 0 days.

(21) Appl. No.: 14/526,703

(22) Filed: Oct. 29, 2014

(65) Prior Publication Data

US 2015/0055135 A1    Feb. 26, 2015

Related U.S. Application Data

(62) Division of application No. 13/962,278, filed on Aug. 8, 2013, now Pat. No. 8,907,438.

(51) Int. Cl.
| | |
|---|---|
| *G01N 21/00* | (2006.01) |
| *G01N 21/63* | (2006.01) |
| *G01N 21/61* | (2006.01) |
| *H01L 51/42* | (2006.01) |
| *H01L 27/30* | (2006.01) |
| *H01L 51/00* | (2006.01) |

(52) U.S. Cl.
CPC ............... *G01N 21/63* (2013.01); *G01N 21/61* (2013.01); *H01L 27/305* (2013.01); *H01L 51/42* (2013.01); *H01L 51/424* (2013.01); *H01L 51/0037* (2013.01); *H01L 51/0038* (2013.01); *H01L 2251/308* (2013.01); *Y02E 10/549* (2013.01)

(58) Field of Classification Search
CPC ....... G01N 21/63; G01N 21/61; H01L 51/448
USPC ................... 356/432–440; 257/431
See application file for complete search history.

(56) References Cited

U.S. PATENT DOCUMENTS

| | | | | |
|---|---|---|---|---|
| 4,164,431 | A  * | 8/1979 | Tang | 136/263 |
| 6,836,332 | B2 * | 12/2004 | Mosley et al. | 356/436 |
| 8,441,090 | B2 * | 5/2013 | Tian et al. | 257/444 |
| 2013/0277649 | A1 | 10/2013 | Gregory et al. | |

* cited by examiner

*Primary Examiner* — Hoa Pham
(74) *Attorney, Agent, or Firm* — Richard J. Kim

(57) ABSTRACT

An organic diode operated in photovoltaic mode is used as a sensor for nitroaromatic electron accepting compounds. While illuminated by a light source with a wavelength within the organic materials absorption the device produces a small photovoltaic response due to inefficient separation of charges. Upon exposure to an electron accepting compound, the device produces an increase in photovoltaic activity due to more efficient charge separation, producing a larger measurable open circuit voltage. Upon removal of the compound the measured voltage decreases and returns to near its baseline value.

9 Claims, 6 Drawing Sheets

METHOD OF SENSING NITROAROMATIC ELECTRON ACCEPTING COMPOUNDS USING A PHOTOVOLTAIC SENSOR

REFERENCE TO RELATED APPLICATIONS

This is a divisional patent application of copending application Ser. No. 13/962,278, filed Aug. 8, 2013, entitled "Semiconducting Organic Photovoltaic Sensor." The aforementioned application is hereby incorporated herein by reference.

GOVERNMENT INTEREST

The invention described herein may be manufactured, used, sold, imported, and/or licensed by or for the Government of the United States of America.

FIELD OF THE INVENTION

This invention relates to organic electronics for gas sensing and more specifically to a device relating photovoltaic activity in an organic device to the presence of electron accepting compounds.

BACKGROUND OF THE INVENTION

An important class of explosive compounds are known as nitroaromatics, such as trinitrotoluene (TNT) and dinitrotoluene (DNT). These compounds are electron accepting compounds due to the addition of the function nitro groups. This property can be exploited by using an electron donating compound and detecting an electron transfer reaction between the nitroaromatic and donor compound. This mechanism has been used for years in systems which optically excite a conjugated polymer and sense a quenching of its photoluminescence upon exposure to nitroaromatics. Research and development of explosive sensing technologies is very active driven by new novel device designs and materials. Besides chemical resistive type devices organic electrical devices are a generally unexplored field in the arena of explosives sensing.

Organic photovoltaics are similar to their inorganic counterparts mainly because they both rely on incident energy (photons) to create excited states which then become separated and collected at electrical contacts. Single layer organic photovoltaics have poor efficiencies due to inefficient charge separation, usually resulting in an excited state returning to its ground state. In recent years researchers have developed heterojunction organic photovoltaics which combine electron donating and electron accepting layers, similar to an inorganic PN junction. In this configuration the excited state electron can transfer from the donating compound to the accepting compound and has a better probability of being collected at the cathode due the lower energy level of the accepting compound.

SUMMARY OF THE INVENTION

This invention uses a single layer organic photovoltaic with a semiconducting conjugated polymer layer. When excited with an ultraviolet light source within its absorption the measured open circuit voltage is small due to the inefficient transfer of charges to the electrodes. Upon exposure to an electron accepting compound such as a nitroaromatic the photovoltaic activity increases producing a larger measured open circuit voltage. This phenomenon can be attributed to the formation of a heterojunction near the cathode where the polymer is exposed to the nitroaromatic. This reaction is reversible when exposure to the compound is removed.

As an exemplary method, an organic diode operated in photovoltaic mode is used as a sensor for nitroaromatic electron accepting compounds. While illuminated by a light source with a wavelength within the organic materials absorption the device produces a small photovoltaic response due to inefficient separation of charges. Upon exposure to an electron accepting compound, the device produces an increase in photovoltaic activity due to more efficient charge separation, producing a larger measurable open circuit voltage. Upon removal of the compound the measured voltage decreases and returns to near its baseline value.

In another aspect, a semiconducting organic photovoltaic sensor device is disclosed. An exemplary semiconducting organic photovoltaic sensor device is comprised of a glass substrate upon which is coated a transparent ITO layer, wherein the transparent ITO layer is used as a positive anode connection; a photoresist layer applied onto a cathode connecting portion of an exposed side of the ITO coating; a semitransparent conducting polymer layer applied onto a sensing portion of said exposed side of the ITO coating; an active polymer layer of the device applied onto an exposed side of said semitransparent conducting polymer layer of said sensing portion; a lithium fluoride layer uniformly applied onto an exposed side of both the photoresist and active polymer layers; and an aluminum layer applied onto an exposed side of said lithium fluoride layer, where a negative cathode connection is provided to the aluminum layer. The layers in between the anode and cathode make up the active layers of the device.

BRIEF DESCRIPTION OF THE DRAWINGS

Additional advantages and features will become apparent as the subject invention becomes better understood by reference to the following detailed description when considered in conjunction with the accompanying drawings wherein.

DETAILED DESCRIPTION

An organic photovoltaic device is used to sense the presence of electron accepting nitroaromatic compounds. The device uses a semiconducting conjugated polymer as the active sensing layer. The polymer layer is excited using a UV light source within its absorption spectrum. Conjugated polymers are electron donators when in their excited state due to the highly delocalized nature of their π-electrons. A device such as a photovoltaic has electrodes with metal work functions defined by the type of metal used. Polymer energy levels are defined by their Highest Occupied Molecular Orbital (HOMO) and Lowest Unoccupied Molecular Orbital (LUMO). An excited state electron may transfer to the lower energy state of the cathode if the energy difference is close. If this transfer is possible the electron will transfer from the polymer LUMO to the cathode creating a free hole able to transfer from the polymer HOMO to the anode. This charge transfer process results in a $V_{OC}$ measurable across the anode and cathode. In single layer organic photovoltaics this transfer typically does not occur do to the lack of an electron acceptor with an intermediate energy level between the polymer LUMO and the cathode work function.

A measurable difference can be observed between a baseline $V_{OC}$ and the $V_{OC}$ when an electron accepting compound is present in the polymer. The presence of an electron acceptor should promote more efficient charge transfer from the polymer to the compound causing the electron to be collected at the electrode. Upon removal of the compound and analyte diffusion out of the polymer the measured $V_{OC}$ should return near its baseline value.

Figure 1:
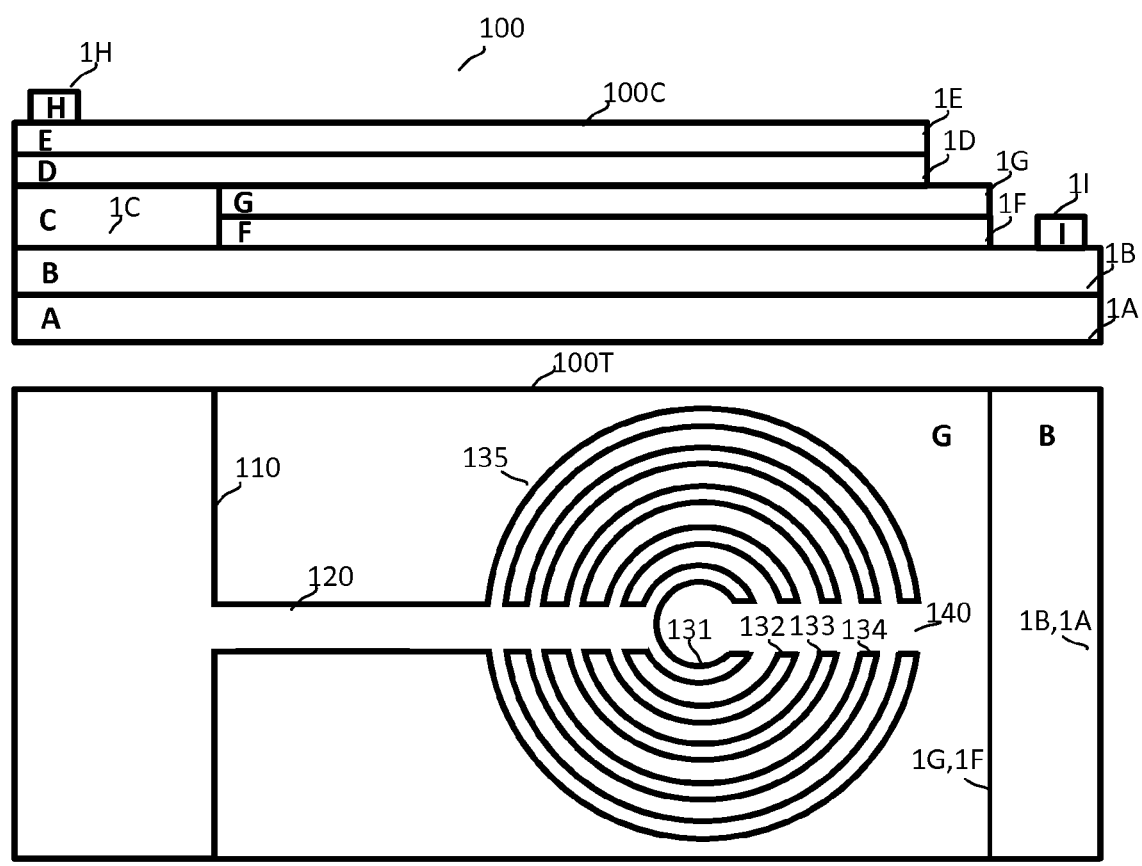
FIG. 1 shows cross-sectional and top views of an exemplary device structure.

FIG. 1 shows cross-sectional 100C and top 100T views of an exemplary device structure 100. Specifically, FIG. 1 shows the design of the cathode exemplified by concentric circles (131-135) providing a large area for charge collection and also a large circumference for diffusion of compounds at the metal polymer interface. Also shown is a cathode column 120 bridging the cathode concentric circles to the cathode pad 110 (shown in its top view 100T) having its cathode connection 1H (shown in its cross-sectional view 100C). Since the bottom substrate is glass 1A coated with transparent Indium Tin Oxide (ITO) 1B the excitation light source can be applied from the bottom. The excitation light excites the PBPV layer 1G where excited state electrons are created. Without an electron accepting compound present the charges have a difficult time transferring to the device anode 1B and cathode (cathode mainly referring to a conductive aluminum layer 1E being shaped together with a lithium fluoride layer 1D below) where they would produce an open circuit voltage. Introducing an electron acceptor such as 1,4DNB as a subject material provides an energy level lower than that of the excited state. The excited state electron now has the option to transfer to this lower energy level and then to the collecting cathode connection. Once the electron has been transferred a hole remains in HOMO level of the polymer where it can now transfer to the anode layer 1B having its anode connection 1I.

FIG. 1 shows a device diagram for the cross section 100C and top view 100T of the sensor. The cross section view is comprised of parts A) Glass, B) Indium Tin Oxide (ITO), C) SU-8 photoresist, D), Lithium Fluoride, E) Aluminum (Al), F) Poly(3,4-ethylenedioxythiophene) poly(styrenesulfonate) (PEDOT:PSS), and G) Poly[2,5-bisoctyloxy)-1,4-phenylenevinylene] (PBPV). The ITO (1B) layer is used as the positive anode connection (1I) and the Al (1E) is used as the negative cathode connection (1H). The layers in between the anode and cathode make up the active layers of the device and will be described in more detail.

Turning now to the top view 100T of FIG. 1, the cathode, characterized as an aluminum layer 1E buffered by a lithium fluoride layer 1D, is configured as a cathode connection pad 110 connected to a series of semi-concentric rings (131-135) via a column 120 of the same materials (1E and 1D). Here, an exemplary set of semi-concentric rings (131-135) are each shown with a gap forming a uniform recess 140. The intent of the semi-concentric rings (131-135) is to maximize points where the active polymer layer (e.g., PBPV layer 1G) interacts with the metal cathode (e.g., aluminum layer 1E via 1D) in order to produce the large area for the analyte to diffuse at this interface. An exemplary semi-concentric ring configuration of the cathode as shown in the top view 100T has five rings (131-135), each with a decreasing diameter in order to fit inside of each other. The diameter of the largest ring 135 is approximately 19 mm, the width of each ring (131-135) is approximately 1.5 mm and the spacing between each ring (131-135) is approximately 1.5 mm. The exemplary recess 140 as shown is optional for ease of shadow mask template generation, but the gap in the rings is not functionally necessary.

Figure 2:
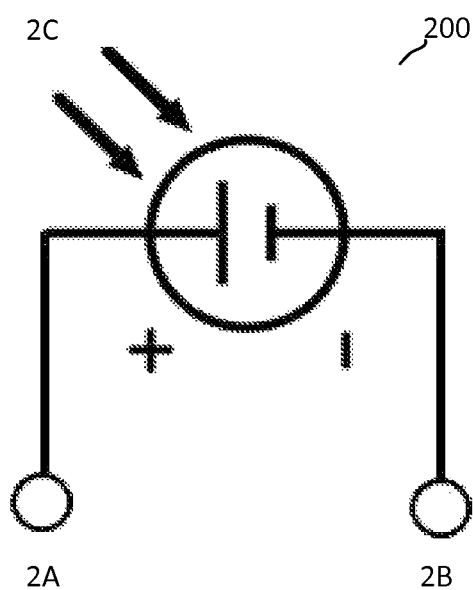
FIG. 2 shows an electrical equivalent of such an exemplary device.

The glass (1A) is used as a physical substrate for the device and is coated with ITO (1B) to provide a transparent conductive layer to be used as the anode. ITO (1B) is a transparent conducting oxide very popular in optoelectronics due to its high conductivity and transparency and hence its use in this design. The SU-8 photoresist (1C) is an epoxy like material applied using standard optical photolithography techniques. It serves to provide a more robust isolation between the anode and cathode to prevent shorting when the cathode connection is made. Lithium fluoride (1D) is an ionic salt which can be used with Aluminum (1E) to create a lower work function metal alloy providing better transfer of electrons to the cathode (e.g., 1H). PEDOT:PSS (1F) is a semitransparent conducting polymer used to better match the energy level of the polymer to the anode interface. The PBPV layer (1G) is the active polymer layer of the device. This is a semiconducting conjugated polymer with an energy gap of ~2.5 eV which can be optically excited with a UV light source. The top view of the device illustrates the concentric ring design of the cathode. This design is accomplished by the use of an evaporation shadow mask of semi-concentric rings (131-135). This cathode design may provide an increased amount of diffusion points at the polymer cathode interface due to the large circumference of the design. FIG. 2 represents the electrical equivalent 200 of the device diagram described in FIG. 1. The circuit symbol represents a photovoltaic device which produces a voltage at terminals 2A and 2B when illuminated by a light source 2C.

Figure 3:
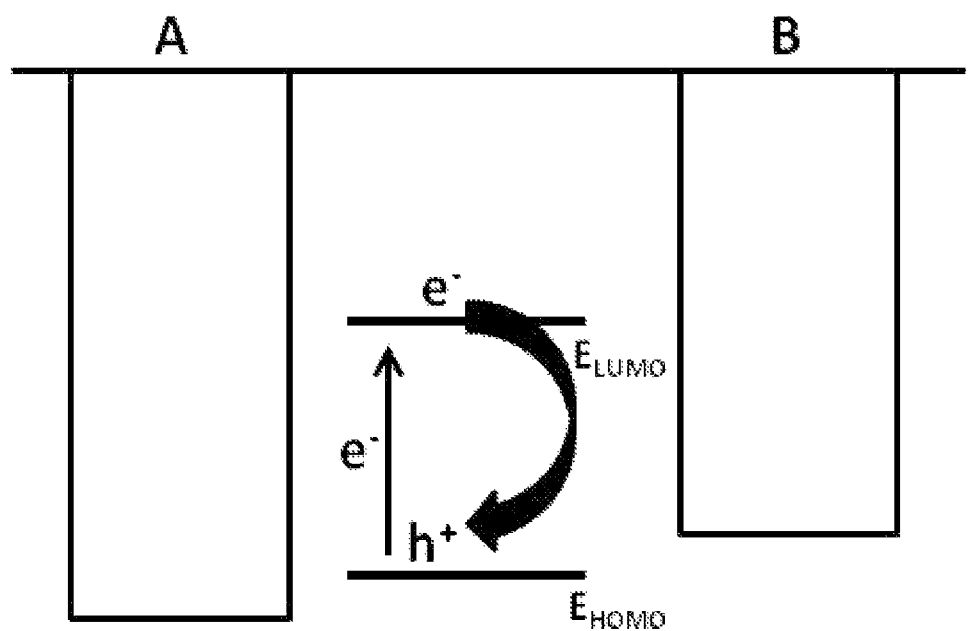
FIG. 3 shows an exemplary energy transfer mechanism in the absence of an electron accepting compound.
Figure 4:
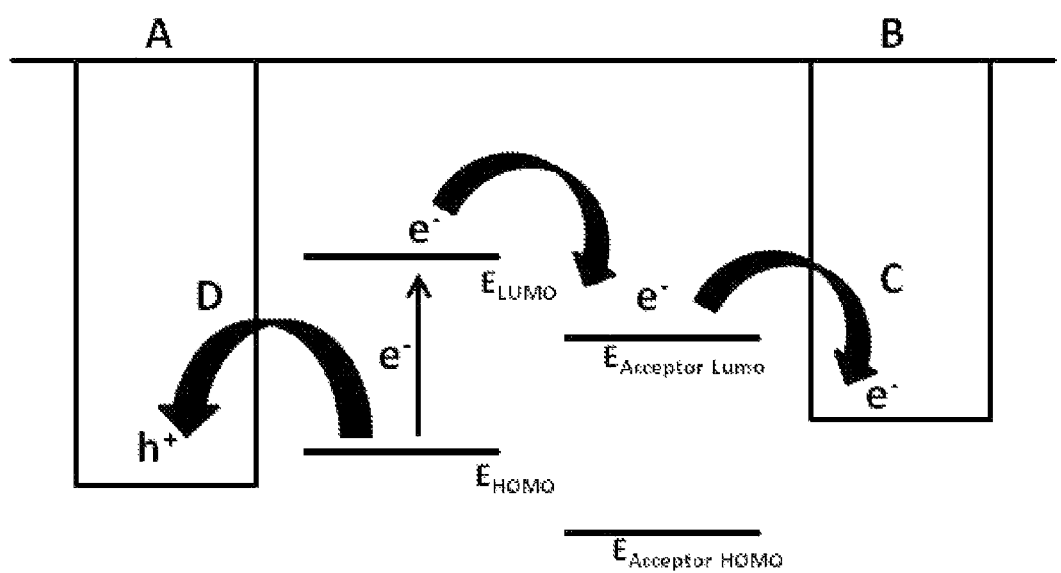
FIG. 4 shows an exemplary energy transfer mechanism in the presence of electron accepting compounds.

FIG. 3 and FIG. 4 detail the internal processes responsible for the seen phenomenon. Specifically, FIG. 3 shows an exemplary energy transfer mechanism in the absence of an electron accepting compound, whereas FIG. 4 shows an exemplary energy transfer mechanism in the presence of electron accepting compounds. In both cases seen in FIG. 3 and FIG. 4 an external excitation light source excites an electron from the polymer $E_{HOMO}$ to $E_{LUMO}$, creating a hole at the $E_{HOMO}$ energy level. At this point the excited state electron at energy level $E_{LUMO}$ can return to its ground state and recombine with the hole, recombine within the energy gap or transfer to another energy level. FIG. 3 represents the condition of the device under normal operation, where an electron accepting compound is not present, resulting in insufficient charge separation and a small open circuit voltage. This may be due to excited state electrons returning from $E_{LUMO}$ to their ground energy state $E_{HOMO}$ or due to recombination with a trap site within the energy gap. Under this condition small amounts of holes are transferred to the anode A and electrons to the cathode B. FIG. 4 represents the condition of the device under operation with an electron accepting compound present. When an electron accepting compound is present, more efficient charge separation is possible due to the lower energy level of the acceptor compound ($E_{Acceptor\ LUMO}$). The electron can more easily transfer from the acceptor compound to the cathode B through this process C. The electron transfer process leaves a hole at $E_{HOMO}$ which is able to transfer to the anode A through process D.

Figure 5:
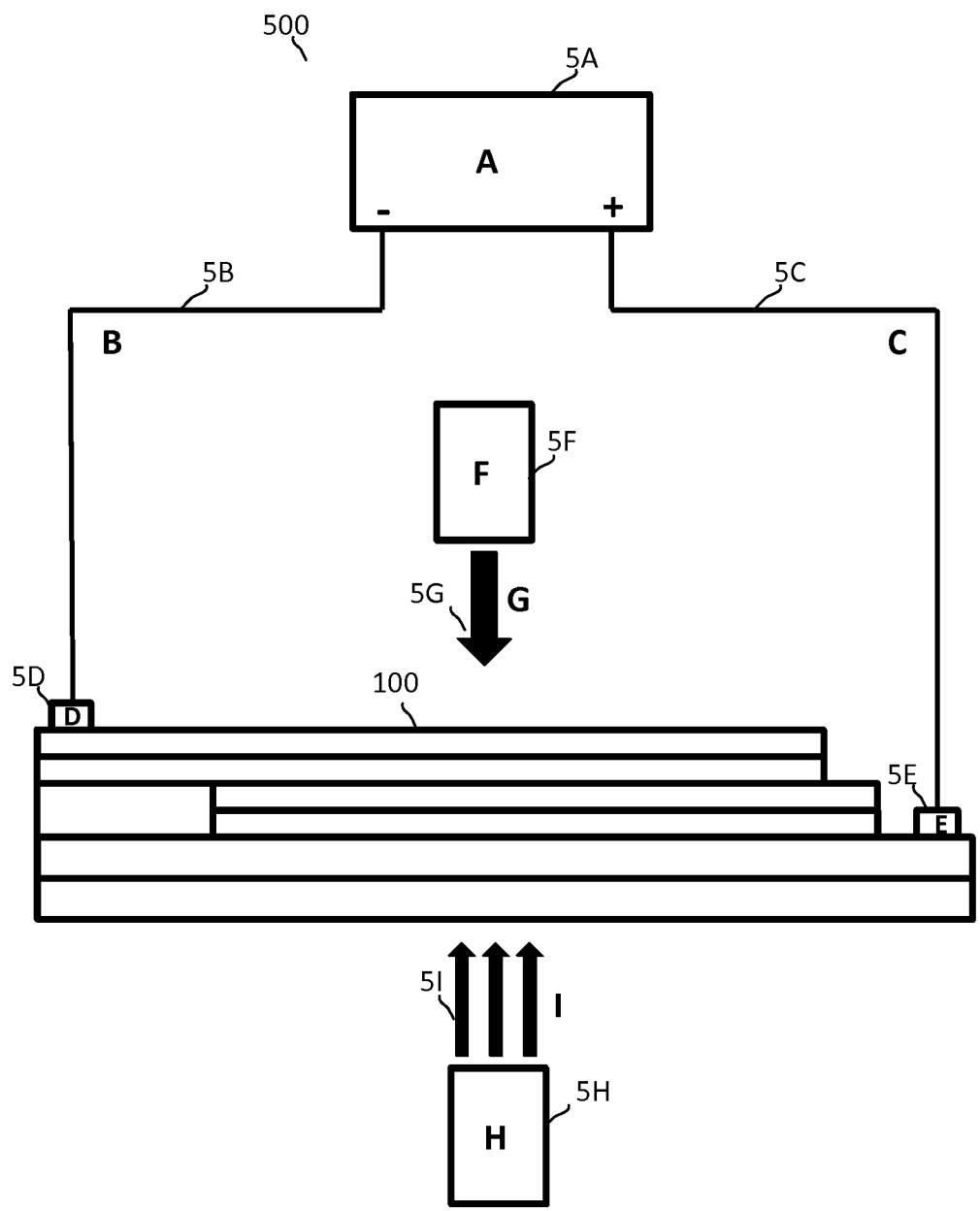
FIG. 5 shows an exemplary measurement system used to test and measure the response of such an exemplary device.

Experimentation was performed with the described device and the electron accepting compound 1,4Dinitrobenzene (1,4DNB). FIG. 5 shows an exemplary setup used to experimentation. Specifically, FIG. 5 shows an exemplary measurement system 500 used to test and measure the response of such an exemplary device 100. A high precision digital multimeter (5A) was used to measure the $V_{OC}$ via electrical leads (5B and 5C). A vapor generator source (5F) was used to generate a gaseous form of 1,4DNB (3G). An ultraviolet (UV) light source (5H) operating at a wavelength of 470 nm (5I) was used to excite the photovoltaic device 100 through the glass substrate. A routine was setup with the vapor source 5F to perform the following flow rates: 1) 400 mL/min of air for 120 s, 2) 300 mL/min 1,4DNB with 100 mL/min air for 180 s, 3) 400 mL/min of air for 180 s. This combination maintains a constant flow rate of 400 mL/min during entire cycle but introduces an amount of 1,4DNB to observe sensor response. FIG. 4 shows an exemplary device response to the parameters described above. The response rises sharply upon exposure to the 1,4DNB from a value of approximately 7.998 mV to a peak value of 28.772 mV giving a change in measured voltage of 20.774 mV. Upon removal of the 1,4DNB the measured voltage returns to near its original baseline voltage value.

FIG. 5 details the configuration of the measurement system used to test the device. Basic testing included the application of an analyte vapor while measuring the open circuit voltage ($V_{OC}$). The measurement system is comprised of a high precision digital multimeter (5A), negative electrical connection (5B), positive electrical connection (5C), Device under test (DUT, 100) cathode connection (5D), DUT anode connection (5E), analyte vapor source (5F), analyte vapor (5G), 470 nm light source (5H), and 470 nm light (5I). The negative connection of the high precision multimeter was connected to the cathode of the DUT while the positive connection was connected to the DUT anode. The 470 nm light source illuminated the sample through the backside glass substrate to excite the active polymer layer. The analyte vapor source was used to generate 1,4Dinitroebnzene (1,4DNB) vapors which were directed at the aluminum cathode.

Figure 6:
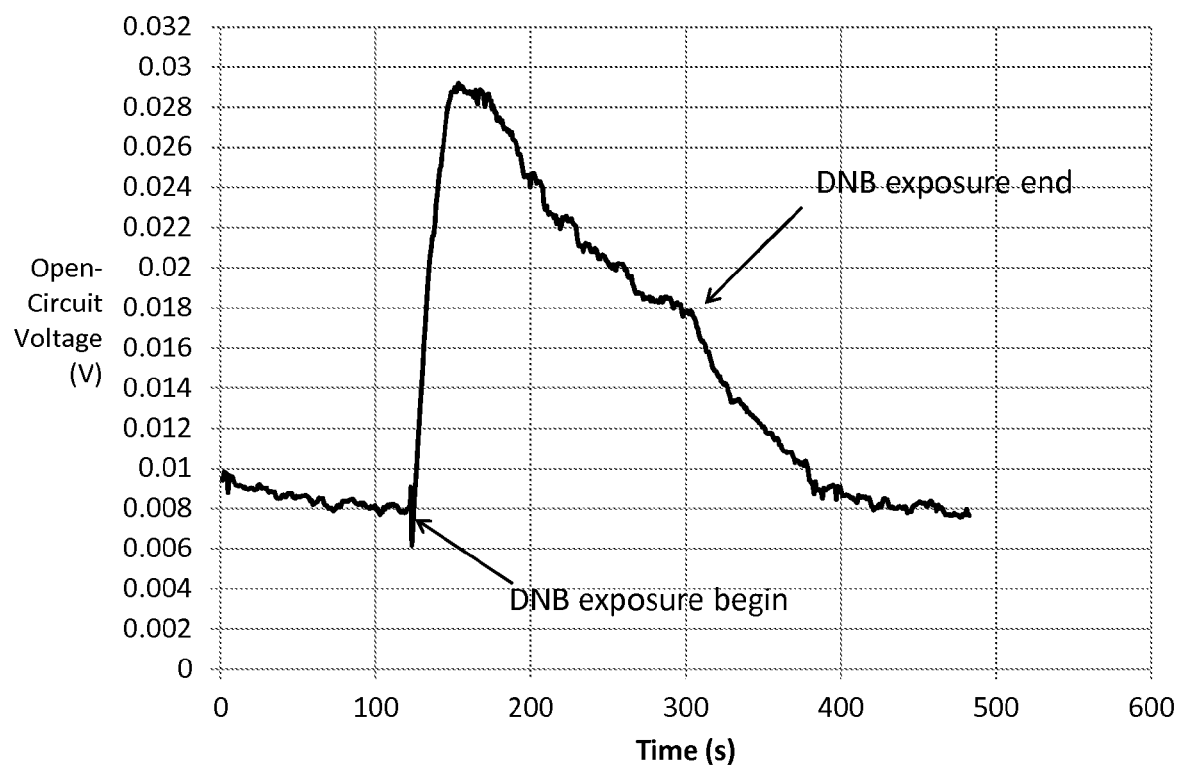
FIG. 6 shows an exemplary measured open circuit voltage in response to 1,4Dinitrobenzene.

To avoid pressure effects, an experiment was performed using an initial flow of 400 mL/min air followed by a combination of 100 mL/min air and 300 mL/min 1,4DNB, always maintaining a constant flow rate. FIG. 6 shows an exemplary measured open circuit voltage in response to 1,4Dinitrobenzene. Specifically, FIG. 6 shows the measured open circuit voltage response of the device while excited by a 470 nm light source and exposed to 1,4DNB at a flow rate of 300 mL/min. Shown in FIG. 6 the 1,4DNB flow began at approximately 120 seconds and was stopped at approximately 300 seconds. When the 1,4DNB exposure begins a sharp increase in open circuit voltage can be seen. The response signal appears to become saturated until the 1,4DNB is removed and signal drops near its initial starting value.

It is obvious that many modifications and variations of the present invention are possible in light of the above teachings. It is therefore to be understood that within the scope of the appended claims, the invention may be practiced otherwise than as described.

What is claimed is:

1. A method of sensing nitroaromatic electron accepting compounds using a photovoltaic sensor, comprising:
   producing an illumination directed towards one side of a subject space using a light source of a wavelength within an absorption spectrum of organic materials;
   disposing said photovoltaic sensor in said subject space such that its glass substrate side faces the light source illumination to produce at least a measurable baseline photovoltaic output in response to said illumination of a wavelength within an absorption spectrum of organic materials;
   disposing a subject material such that analyte vapor is emitted within said subject space; and
   detecting a photovoltaic output measurably greater than said baseline photovoltaic output in the presence of an electron accepting compound in said analyte vapor as a result of said photovoltaic sensor producing an increase in photovoltaic activity in the presence of an electron accepting compound.

2. The method according to claim 1, wherein said photovoltaic sensor is an organic diode operated in photovoltaic mode.

3. The method according to claim 2, wherein production of said measurable baseline photovoltaic output is due to inefficient separation of charges of said organic diode operated in photovoltaic mode.

4. The method according to claim 1, wherein said subject material is comprised of one or more nitroaromatic electron accepting compounds.

5. The method according to claim 1, wherein a measurably small baseline level of photovoltaic output in response to said illumination of a wavelength within an absorption spectrum of organic materials occurs in the absence of a nitroaromatic electron accepting compound in said subject space.

6. The method according to claim 1, wherein said photovoltaic output measurably greater than said baseline photovoltaic output occurs when one or more nitroaromatic electron accepting compounds is present in said subject space.

7. The method according to claim 1, wherein said photovoltaic sensor produces an increase in photovoltaic activity due to more efficient charge separation in the presence of an electron accepting compound.

8. The method according to claim 1, wherein said light source is a 470 nm light source which illuminates the subject space through the glass substrate side to excite an active polymer layer of said photovoltaic sensor.

9. The method according to claim 1, wherein said analyte vapor contains 1,4Dinitroebnzene.

* * * * *